United States Patent [19]

Narayanan et al.

[11] Patent Number: 5,057,088
[45] Date of Patent: Oct. 15, 1991

[54] NEEDLE GUARD

[76] Inventors: Krishna Narayanan, 423 N. St. Clair, Pittsburgh, Pa. 15206; Eugene D. Ross, 511 2nd St., Southampton, Pa. 18966

[21] Appl. No.: 235,101

[22] Filed: Aug. 23, 1988

[51] Int. Cl.⁵ .............................................. A61M 5/32
[52] U.S. Cl. .................................... 604/198; 604/263
[58] Field of Search ............... 604/198, 199, 197, 263

[56] References Cited

U.S. PATENT DOCUMENTS

| | | | |
|---|---|---|---|
| 4,498,902 | 2/1985 | Ash et al. | 604/281 |
| 4,695,274 | 9/1987 | Fox | 604/263 |
| 4,702,739 | 10/1987 | Milorad | 604/198 |
| 4,747,836 | 5/1988 | Luther | 604/198 |

FOREIGN PATENT DOCUMENTS 2202740 10/1988 United Kingdom ............... 604/198

Primary Examiner—Stephen C. Pellegrino
Attorney, Agent, or Firm—Robert S. Beiser

[57] ABSTRACT

An improved needle guard for a syringe is provided having a tubular body. The needle guard includes a longitudinal bore and one or more slots or slits formed therein. The longitudinal bore of the guard is sized for telescopic reception of and contraction about the tubular body of the syringe. Slots or slits are arranged so as to allow deformation of the longitudinal bore of the needle guard thereby increasing the inside diameter of the longitudinal bore so as to allow axial movement of the needle guard along the tubular body of the syringe.

18 Claims, 1 Drawing Sheet

NEEDLE GUARD

BACKGROUND OF THE INVENTION

It is extremely common for health care workers to accidentally stick themselves with hypodermic needles during use. Such accidental needle exposures can result in transmission of hepatitis and potentially acquired immune deficiency syndrome—AIDS as well as other communicable diseases. Accidental needle sticks often occur when a blood drawer or any health care professional administering an injection attempts to recap a needle after use or leaves a contaminated exposed needle on work surfaces which may accidentally injure somebody.

The use of hypodermic syringes and needle protectors therefore is widely known. Conventionally, needles are made with hubs and sockets adapted to be attached to the distal end of a syringe. A molded plastic cap is secured to the hub of the needle. This plastic cap is removable to expose the needle for use.

Alternatively, syringes are provided in which the needle is integrally formed as part of the syringe. Again needle guards are provided with the syringe and which are removed prior to use.

A number of attempts have been made in the past to overcome the dangers involved in the use of hypodermic, syringes. The following U.S. Pat. Nos. represent several of these attempts:

| | | | |
|---|---|---|---|
| 4,643,200 | Jennings | 253,426 | Australia |
| 4,573,975 | Frist | WO 85/03006 | |
| 4,610,667 | Pedicano | | |
| 4,654,034 | Masters | | |
| 4,742,910 | Staebler | | |
| 4,743,233 | Schneider | 4,731,059 | Wanderer |
| 4,725,267 | Vaillancourt | 4,723,943 | Spencer |
| 4,664,259 | Landis | 4,659,330 | Nelson |
| 4,643,722 | Smith | 4,634,428 | Cuu |
| 4,631,057 | Mitchell | 4,425,120 | Sampson |
| 4,345,822 | Winstead-Hall | 3,073,306 | Linder |

Of particular interest is U.S. Pat. No. 4,742,910, which shows a shield having a sheath attached thereto with an elastic cover which is penetrated by the syringe. While the shield is elastic, the body of the sheath is rigid.

U.S. Pat. No. 4,643,200 discloses a sheath having a longitudinal slot. However, the sheath is rigid and the slot is used for interlocking with a pin on the syringe.

U.S. Pat. No. 4,725,267, Vaillancourt, discloses an elastic shield which is compressible in the longitudinal direction and loosely circumscribes the syringe. The shield extends when released from attachment to the syringe. The shield does not slide along the syringe itself.

U.S. Pat. No. 4,723,943 discloses a sheath having a longitudinal slot. Again, however, the sheath is rigid.

U.S. Pat. No. 4,664,259 discloses a sheath which is bifurcated. The sheath has elastic hinges for holding the sheath away from the needle. However, the sheath does not slide along the barrel of the syringe.

U.S. Pat. No. 4,659,330 discloses a sheath which is attached to a syringe by means of a clip. The clip has an elastic ring which fits about the syringe. The clip is similar in design to clips commonly found on pens. The body of the tubular sheath does not clip or attach onto the syringe body.

U.S. Pat. No. 4,643,722 again shows a sheath having a longitudinal slot. However, the sheath is rigid and the sheath is designed for longitudinal insertion of the needle of the syringe.

Despite the abundance of sheath guards in the prior art, as evidenced by the above listed patents, the low cost easy to use needle sheath remains an elusive goal.

SUMMARY OF THE INVENTION

Accordingly, it is an object of the present invention to provide a low cost, easy to use needle guard for syringes to prevent inadvertently sticking the needle into the patient or nurse or other medical professional during use.

It is an additional object of the present invention to provide a needle guard which fits easily over a number of different sized syringes.

The present invention relates generally to hypodermic syringes and more particularly to needle guards for hypodermic syringes which prevent inadvertent contact of the needle with the patient or the medical professional utilizing the syringe.

In a preferred embodiment, the hypodermic syringe itself has a hollow barrel, a plunger slidably movable within the barrel and a hypodermic needle extending from end of the syringe. An elastic thermoplastic sleeve circumscribes the barrel and extends from the barrel over the needle. The sleeve has a longitudinal slot along one side and is sufficiently resilient so as to grip the barrel of the syringe thereby remaining fixedly positioned on the syringe even when coming into contact with the patient or another surface. However, the thermoplastic sleeve is deformable along the longitudinal slot so that when manual pressure is applied against the sleeve the sleeve may be moved backwardly along the barrel of the syringe thereby exposing the needle for use. In a preferred embodiment the sleeve may be utilized for protecting syringes of a number of different sizes and may be easily manufactured using conventional extrusion technology.

These and other objects of the invention will become apparent from the following specification.

A BRIEF DESCRIPTION OF THE DRAWINGS

FIG. 1 of the drawings is a top view of a syringe having a conventional needle guard thereon, as disclosed in the prior art.

FIG. 2 of the drawings is a front perspective view of a syringe and needle guard of the present invention.

FIG. 3 of the drawings is a front perspective view of the needle guard of FIG. 2 shown in a distended configuration.

FIG. 4 of the drawings is a top view of the needle guard and sheath of FIG. 2 with the sheath shown in an extended position.

FIG. 5 of the drawings is a top view of the needle guard and sheath of FIG. 2 with the sheath shown in a retracted position.

DETAILED DESCRIPTION OF THE PREFERRED EMBODIMENT

Figure 1:
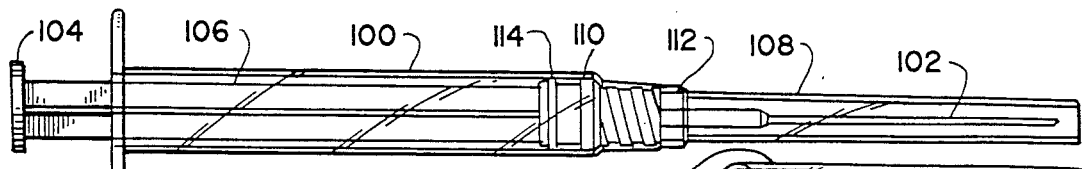

As shown in FIG. 1 of the drawings, in the prior art, it is conventional to have a syringe 100 having a needle 102 extending distally therefrom. Syringes conventionally have a plunger 104 extending into the longitudinal bore 106 of the syringe 100. A sheath guard 108 is conventionally attached to the distal end 110 of the syringe 100 by means of flanges 112 which extend from the distal end and which interlock with tubular receiving portion 114 of the sheath guard 108.

Figure 2:
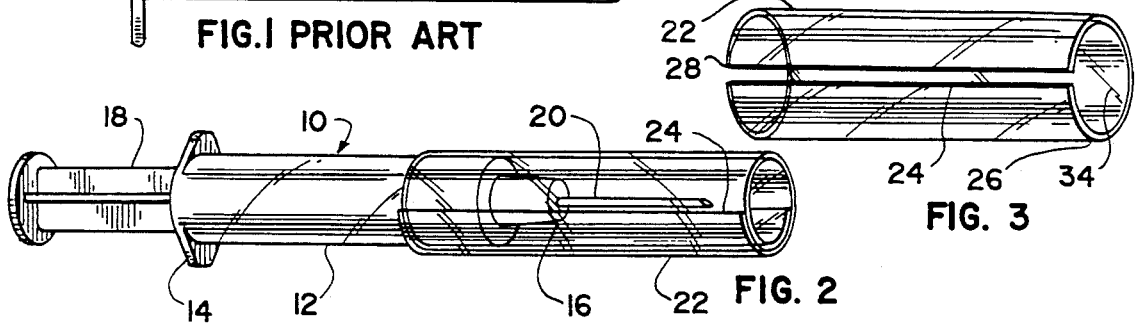
Figure 4:
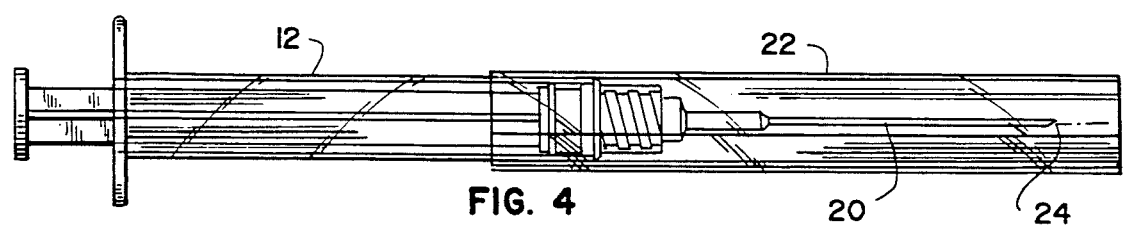

In the present invention, (as shown in FIG. 2), a syringe 10 comprises a hollow barrel member 12 having a first end 14 and second end 16 respectively at the proximal and distal ends of the syringe 10. A plunger 18 is slidably movable within the barrel member 12 and extends from the first end 14 of the barrel member 12. A hypodermic needle 20 is mounted on and extends axially outward from the second opposite end 16 of barrel member 12. A sleeve member 22 encircles a portion of the barrel member 12 and is slidably movable between a first position, (best shown in FIG. 4) with the needle 20 contained from the sleeve 22. A second position, (best shown in FIG. 5) is characterized by the needle 20 extending from the sleeve 22, and also shown in FIG. 2.

As further shown in FIG. 2, sleeve or sheath 22 comprises a thermoplastic tube having a longitudinal slot 24 along one side thereof. The thermoplastic tube 22 is constructed of an elastic and resilient thermoplastic material such as polyethylene or polypropylene among others, which grips the barrel 12 of the syringe as to remain fixedly positioned thereon. In addition, the thermoplastic sleeve 22 is sufficiently elastic to allow the sleeve 22 to be manually slid from the first position, shown in FIG. 5 to the second position shown in FIG. 4. As a result, accidental contact with the needle 20 by the medical professional is prevented when the sleeve is in the first position. As further shown in the drawings, in a preferred embodiment the sleeve 22 is preferably transparent. However, in order to insure that the position of the sleeve is known by the user, portions of the sleeve may be printed or colored as desired.

Figure 3:
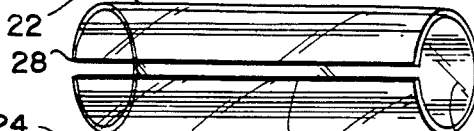
Figure 5:
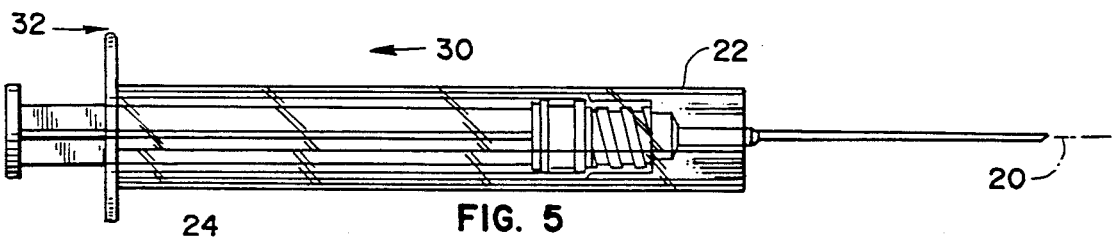

As best shown in FIG. 3 of the drawings, a slit or slot 24, in a preferred embodiment, runs longitudinally from the first end 26 to the second end 28 of sleeve 22. Tube 22 and slit 24 are constructed and arranged so that axial force as best shown by arrow 30 in FIG. 5 may be applied against tube 22 along towards barrel member 12. When countervailing force, as shown in FIG. 5 by arrow 32, is applied against barrel member 12, sleeve 22 is deformed along longitudinal slot 24. As a result, the inside diameter 34, best shown in FIG. 3, tube 22 is increased so as to allow axial movement of tube 22 from the first position in FIG. 4 to the second position shown in FIG. 5.

Figure 6:
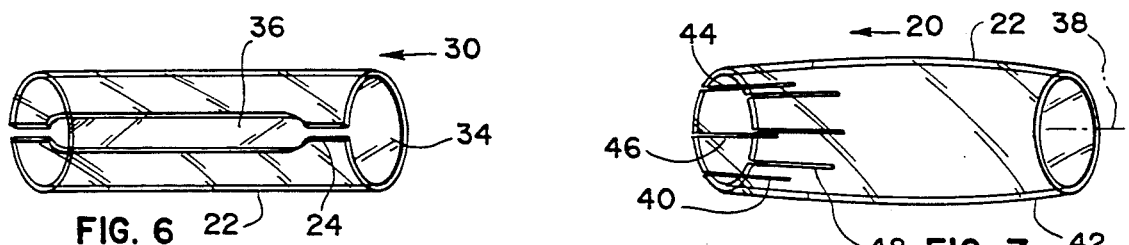
FIG. 6 is a top view of an alternate embodiment of the invention showing a tubular thermoplastic sheath having an oblong shaped longitudinal slot extending longitudinally thereon.

As seen in FIG. 6, in an alternate embodiment of the invention, an oblong opening slot 24 having an oblong opening 36 extends longitudinally along tube 22. Oblong opening 36 is sized so that when axial force is applied in the longitudinal direction 30 toward barrel 12 and barrel 12 is pushed in the opposite direction 32, this causes the tube 22 to deform so that inside diameter 34 of said tube 22 is increased so as to allow axial movement of the tube 22 from the first position shown in FIG. 4 to the second position shown in FIG. 5. Thus the needle 20 is exposed. Alternatively, sleeve 22 can be extended back over needle 20 by reversing the direction in which force is applied.

Figure 7:
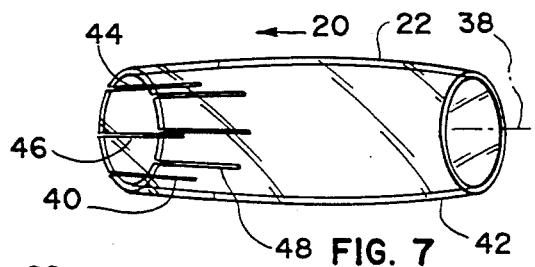
FIG. 7 is a top view of an additional alternate embodiment of the invention showing a plurality of slots proximate one end of the sheath as to allow deformation of the need for sliding along the syringe.
Figure 8:
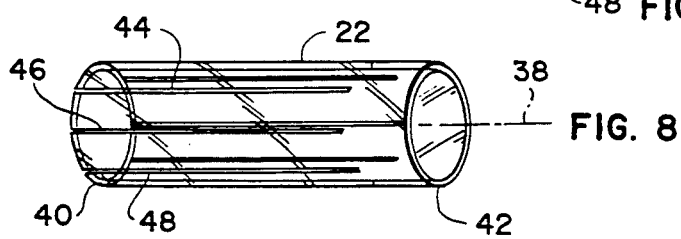
FIG. 8 is a top view of another alternate embodiment of the invention showing a plurality of slots formed along the length of the sheath so as to allow deformation of the sheath for movement along the syringe.

As shown in FIG. 7 of the drawings, in an additional alternative embodiment, tube 22 includes an axial bore 38 which extends therethrough. Axial bore 38 is also found in the other embodiments of the invention. Axial bore 38 has a smaller diameter proximate the proximal end 40 and distal end 42 of tube 22. Tube 22 tightly conforms to the barrel 12 of the syringe 10. One or more slots, such as slots 44, 46 and 48 are formed in the tube 22 proximate proximal end 40. As a result, when axial force is applied along axis 30, tube 22 may be slid along barrel 12.

Tube 22 may be constructed of thermoplastic or other materials such as polyethylene, polypropylene, nylon, polyester, polystyrene, thermoplastic elastomers, vinyl polymers and copolymers or polycarbonate. Other conventional elastic and thermoplastic materials may also be utilized. However, in a preferred embodiment, as shown in FIG. 3, tube 22 may be constructed of either an extruded or injection molded tube of plastic material having the slot 24 formed therein during manufacture.

As mentioned above, tube 22 must be sufficiently elastic so as to allow deformation and yet sufficiently resilient so as to tightly grip the barrel 12. Although a wide array of materials are available, it may be said generally that the modulus of elasticity of the tubular thermoplastic member 22 is from 8 to $500 \times 10^3$ pounds per square inch. This range encompasses virtually all known thermoplastic materials. Similarly, the thermoplastic material must no break when distended. Accordingly, the tensile strength of the tubular thermoplastic member 22 is from 10 to 440 pounds per square inch. In a preferred embodiment, the tubular sleeve 22 may be from 2 to as much as 50 mils in thickness. The tubular sleeve must be thick enough to withstand impact against the user or a work surface deforming. At the same time, the tubular sleeve must be sufficiently elastic so as to deform when pressed in the axial direction against the barrel 12.

Figure 9:
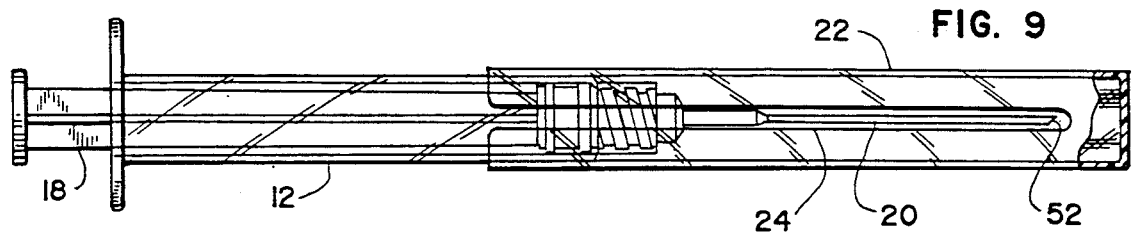
FIG. 9 is a top view of another alternate embodiment of the invention showing a sheath closed at a first end proximate the tip of the needle.

As shown in FIG. 9, in one embodiment tubular sleeve 22 may be closed at a first end 50 proximate the tip 52 of needle 20. As a result, inadvertent contact with the needle tip 52 is prevented.

Thus, in accordance with the present invention, an improved needle guard for a syringe is provided which is relatively simple in construction and operation and thereby economical to manufacture, thus lending itself to disposal after completion of the medical procedure required.

While preferred embodiments of the present invention have been illustrated and described herein, it will be understood that changes and modifications may be made therein without departing from the scope of the invention. Various features of the invention are defined in the following claims.

What is claimed is:

1. A hypodermic syringe for giving injections comprising:
   a hollow barrel member with first and second opposite ends;
   a plunger, slidably movable within said barrel member and extending from said first barrel end;

a hypodermic needle mounted on and extending axially outward from said second opposite end of said barrel;

a sleeve encircling a portion of said barrel and slidably movable between a first position being characterized by said needle being contained within said sleeve and a second position being characterized by said needle projecting from said sleeve;

said sleeve comprising a thermoplastic tube having a longitudinal slot along one side, said thermoplastic tube being constructed of an elastic and resilient thermoplastic material which grips said barrel of said syringe so as to remain fixedly positioned thereon, said thermoplastic sleeve being sufficiently elastic to allow said sleeve to be manually slid from said first position to said second position on said barrel; whereby accidental contact with said needle is prevented by said sleeve when said sleeve is in said first position.

2. A syringe as claimed in claim. 1 wherein at least a portion of said sleeve is transparent.

3. The hypodermic syringe of claim 1, wherein said slot comprises a longitudinal slit through said thermoplastic material and along the entire length of said tube, wherein said slit provides flexibility to said tube so that axial force applied against said tube toward said barrel in combination with countervailing force applied along said barrel toward said sleeve is effective to deform said tube thereby increasing the diameter of said tube so as to allow axial movement of said tube from said first position to said second position.

4. The syringe of claim 1 wherein said slot comprises an oblong opening along one side of said tube, said opening being sized so that axial force applied against said tube toward said barrel in combination with countervailing force applied along said barrel toward said sleeve is effective to deform said tube thereby increasing the diameter of said tube so as to allow axial movement of said tube from said first position to said second position.

5. The syringe of claim 1 wherever said tube has an axial bore extending therethrough, said bore being of smaller diameter proximate the proximal and distal ends of said tube so as to tightly conform to said barrel, said slot being positioned proximate said proximal end of said tube so that said proximal end of said tube deforms when axial force is applied along said tube toward said barrel and countervailing force is applied along said barrel toward said tube, thereby increasing the inside diameter of said proximal end of said tube so as to allow said tube to be moved from said first position to said second position.

6. The syringe of claim 1 wherein said thermoplastic comprises polyethylene.

7. The syringe of claim 1 wherein said thermoplastic comprises polypropylene.

8. The syringe of claim 1, wherein said tube comprises a plurality of slits formed in said tube, said slits being formed through said tube and extending from one end thereof in a longitudinal direction along a partial length of said tube so as to deform when axial force is applied along said tube toward said barrel and countervailing force is applied along said barrel toward said tube whereby said tube is deformed so as to allow movement of said tube from said first position to said second position.

9. The syringe of claim 1 wherein said tube comprises an extruded elastic tubular thermoplastic member.

10. The needle guard of claim 1 wherein the modules of elasticity of said tubular thermoplastic member from 8 to 500. $\times 10^3$ pounds per square inch.

11. The needle guard of claim 1 wherein the tensile strength of said tubular thermoplastic member is 10–440 pounds per square inch.

12. The needle guard of claim 1 wherein said tubular thermoplastic member comprises one or more of the group consisting of:

nylon, polyester, polyethylene, polybutylene, polypropylene, polystyrene, thermoplastic elastomers, vinyl polymers and copolymers or polycarbonate.

13. The needle guard of claim 1 wherein said tubular thermoplastic member is sufficiently elastic to fit the longitudinal bore of said tubular thermoplastic member over a range of sizes of syringes having differing outside diameters.

14. The needle guard of claim 1 wherein said sleeve is from two mils to 20 mils in thickness.

15. The syringe of claim 1 wherein said tube comprises an injection molded tubular thermoplastic member.

16. A hypodermic syringe for giving injections comprising:

a hollow barrel member with first and second opposite ends;

a plunger, slidably movable within said barrel member and extending from said first barrel end;

a hypodermic needle mounted on and extending axially outward from said second opposite end of said barrel;

a sleeve encircling a portion of said barrel and slidably movably between a first position being characterized by said needle being contained within said sleeve and a second position being characterized by said needle projecting from said sleeve;

said sleeve comprising a thermoplastic tube having a longitudinal slot along one side, said thermoplastic tube being constructed of an elastic and resilient thermoplastic material which grips said barrel of said syringe so as to remain fixedly positioned thereon, said thermoplastic sleeve being sufficiently elastic to allow said sleeve to be manually slid from said first position to said second position on said barrel;

whereby accidental contact with said needle is prevented by said sleeve when said sleeve is in said first position; and wherein said slot further comprises a longitudinal slit through said thermoplastic material and along the entire length of said tube, wherein said slit provides flexibility to said tube so that axial force supplied against said tube towards said barrel in combination with countervailing force applied along said barrel toward said sleeve is effective to deform said tube thereby increasing the diameter of said tube so as to allow axial movement of said tube from said first position to said second position.

17. A hypodermic syringe for giving injections comprising:

a hollow barrel member with first and second opposite ends;

a plunger, slidably movable within said barrel member and extending from said first barrel end;

a hypodermic needle mounted on and extending axially outward from said second opposite end of said barrel;

a sleeve encircling a portion of said barrel and slidably movably between a first position being characterized by said needle being contained within said sleeve and a second position being characterized by said needle projecting from said sleeve;

said sleeve comprising a thermoplastic tube having a longitudinal slot along one side, said thermoplastic tube being constructed of an elastic and resilient thermoplastic material which grips said barrel of said syringe so as to remain fixedly positioned thereon, said thermoplastic sleeve being sufficiently elastic to allow said sleeve to be manually slid from said first position to said second position on said barrel;

whereby accidental contact with said needle is prevented by said sleeve when said sleeve is in said first position; and wherein said slot further comprises an oblong opening along one side of said tube, said opening being sized so that axial force applied against said tube towards said barrel in combination with countervailing force applied along said barrel toward said sleeve is effective to deform said tube thereby increasing the diameter of said tube so as to allow axial movement of said tube from said first position to said second position.

18. A hypodermic syringe for giving injections comprising:

a hollow barrel member with first and second opposite ends;

a plunger, slidably movable within said barrel member and extending from said first barrel end;

a hypodermic needle mounted on and extending axially outward from said second opposite end of said barrel;

a sleeve encircling a portion of said barrel and slidably movably between a first position being characterized by said needle being contained within said sleeve an a second position being characterized by said needle projecting from said sleeve;

said sleeve comprising a thermoplastic tube having a longitudinal slot along one side, said thermoplastic tube being constructed of an elastic and resilient thermoplastic material which grips said barrel of said syringe so as to remain fixedly positioned thereon, said thermoplastic sleeve being sufficiently elastic to allow said sleeve to be manually slid from said first position to said second position on said barrel;

whereby accidental contact with said needle is prevented by said sleeve when said sleeve is in said first position; and wherein said tube further has an axial bore extending therethrough, said bore being of smaller diameter proximate the proximal and distal ends of said tube so as to tightly conform to said barrel, said slot being positioned proximate said proximal end of said tube so that said proximal end of said tube deforms when axial force is applied along said tube towards said barrel and counter vailing force is applied along said barrel toward said tube, thereby increasing the inside diameter of said proximal end of said tube so as to allow said tube to be removed from said first position to said second position.

* * * * *